(12) United States Patent
Govari et al.

(10) Patent No.: US 7,918,850 B2
(45) Date of Patent: Apr. 5, 2011

(54) LESION ASSESSMENT BY PACING

(75) Inventors: Assaf Govari, Haifa (IL); Andres Claudio Altmann, Haifa (IL); Yaron Ephrath, Karkur (IL)

(73) Assignee: Biosense Wabster, Inc., Diamond Bar, CA (US)

( * ) Notice: Subject to any disclaimer, the term of this patent is extended or adjusted under 35 U.S.C. 154(b) by 907 days.

(21) Appl. No.: 11/357,512

(22) Filed: Feb. 17, 2006

(65) Prior Publication Data

US 2007/0198007 A1 Aug. 23, 2007

(51) Int. Cl.
*A61B 18/18* (2006.01)

(52) U.S. Cl. .......................... 606/34; 606/41

(58) Field of Classification Search .............. 606/32, 606/34, 41
See application file for complete search history.

(56) References Cited

U.S. PATENT DOCUMENTS

| | | | |
|---|---|---|---|
| 5,295,484 A * | 3/1994 | Marcus et al. | 600/439 |
| 5,366,490 A | 11/1994 | Edwards et al. | |
| 5,443,489 A | 8/1995 | Ben-Haim | |
| 5,480,422 A | 1/1996 | Ben-Haim | |
| 5,807,395 A | 9/1998 | Mulier et al. | |
| 5,938,660 A | 8/1999 | Swartz et al. | |
| 5,954,665 A | 9/1999 | Ben-Haim | |
| 5,971,983 A | 10/1999 | Lesh | |
| 5,991,660 A * | 11/1999 | Goyal | 607/14 |
| 6,004,269 A | 12/1999 | Crowley et al. | |
| 6,027,500 A * | 2/2000 | Buckles et al. | 606/34 |
| 6,064,902 A | 5/2000 | Haissaguerre et al. | |
| 6,083,170 A | 7/2000 | Ben-Haim | |
| 6,090,084 A | 7/2000 | Hassett et al. | |
| 6,117,101 A | 9/2000 | Diederich et al. | |
| 6,164,283 A | 12/2000 | Lesh | |
| 6,190,382 B1 | 2/2001 | Ormsby et al. | |
| 6,235,025 B1 | 5/2001 | Swartz et al. | |
| 6,245,064 B1 | 6/2001 | Lesh et al. | |
| 6,251,109 B1 | 6/2001 | Hassett et al. | |
| 6,301,496 B1 | 10/2001 | Reisfeld | |
| 6,305,378 B1 | 10/2001 | Lesh | |
| 6,321,109 B2 | 11/2001 | Ben-Haim et al. | |
| 6,332,089 B1 | 12/2001 | Acker et al. | |
| 6,618,612 B1 | 9/2003 | Acker et al. | |
| 6,669,692 B1 | 12/2003 | Nelson et al. | |
| 6,690,963 B2 | 2/2004 | Ben-Haim et al. | |

(Continued)

FOREIGN PATENT DOCUMENTS

EP 1398056 A1 3/2004

(Continued)

OTHER PUBLICATIONS

Botteron, G.W., M.D. et al. "A Technique for Measurement of the Extent of Spatial Organizational Atrial Fibrillation in the Intact Human Heart", IEEE Transacation on, vol. 42, Issue 6, Jun. 1995 pp. 579-586. (Abstract).

(Continued)

*Primary Examiner* — Linda C Dvorak
*Assistant Examiner* — Amanda Scott
(74) *Attorney, Agent, or Firm* — Louis J. Capezzuto (57) ABSTRACT

Monitoring intracardiac ablation progress in near real time is accomplished by evaluating capture of a pacing signal while ablation energy is concurrently directed to a target site. Sufficiency of ablation is indicated by failure of signal capture at a maximum predetermined pacing voltage. A common electrode in a cardiac catheter is simultaneously used to test pacing capture and to deliver ablation energy.

13 Claims, 5 Drawing Sheets

U.S. PATENT DOCUMENTS

| | | |
|---|---|---|
| 6,743,225 B2 | 6/2004 | Sanchez et al. |
| 6,751,492 B2 | 6/2004 | Ben-Haim |
| 2002/0065455 A1 | 5/2002 | Ben-Haim et al. |
| 2002/0091383 A1 | 7/2002 | Hooven |
| 2002/0111619 A1* | 8/2002 | Keast et al. ............... 606/41 |
| 2003/0171743 A1* | 9/2003 | Tasto et al. ............... 606/32 |
| 2004/0068178 A1 | 4/2004 | Govari |
| 2004/0143258 A1 | 7/2004 | Fuimaono |
| 2004/0147920 A1 | 7/2004 | Keidar |
| 2004/0158141 A1 | 8/2004 | Scheib |
| 2005/0099290 A1 | 5/2005 | Govari |
| 2005/0148892 A1* | 7/2005 | Desai ...................... 600/510 |

FOREIGN PATENT DOCUMENTS

| | | |
|---|---|---|
| EP | 1415608 A2 | 5/2004 |
| EP | 1415608 A3 | 10/2004 |
| GB | 2267035 A | 11/1993 |
| WO | WO 94/15528 | 7/1994 |

OTHER PUBLICATIONS

Botteron, G.W., M.D. et al. "Quantitative Assessment of the Spatial Organization of Atrial Fibrillation in the Intact Human Heart", Circulation 93 (Feb. 1, 1996), pp. 513-518.

Natale, A., M.D., "First Human Experience with Pulmonary Vein Isolation Using a Through-the-Balloon Circumferential Ultrasound Ablation System for Recurrent Atrial Fibrillation", Circulation, 2000;102:1879-1882.

Pappone, C., M.D., PhD. "Circumferential Radiofrequency Ablation of Pulmonary Vein Ostia", Circulation, 2000;102:2619-2628.

EP Search Report 07250656.1 dated May 14, 2007.

* cited by examiner

LESION ASSESSMENT BY PACING

BACKGROUND OF THE INVENTION

1. Field of the Invention

This invention relates to methods and systems for the treatment of conduction disturbances of the heart. More particularly, this invention relates to validating and monitoring percutaneous cardiac ablation procedures.

2. Description of the Related Art

Atrial fibrillation is a well-known disorder of the heart, which causes hemodynamic efficiency to be reduced and which, in serious cases, can lead to cardiac embolization, stroke, ventricular arrhythmias and other potentially fatal complications. Atrial fibrillation is frequently engendered by abnormal electrical conduction paths within the heart muscle. Normally, electrical activation signals are conducted in an orderly way through the atrium and into the ventricle, passing each point in the heart only once in each heart cycle. Electrical activation signals at different locations in the heart are well correlated, taking into account normal propagation delays from one region of the heart to another. In response to local activation signals, the atrial muscle fibers contract in proper synchrony, to pump blood through the atrium. In atrial fibrillation, however, this orderly contraction is lost, it is believed, as multiple, changing, spatially disorganized activation wavelets sweep across the surface of the atria, resulting in irregular patterns of electrical activation. A given atrial muscle fiber is activated to contract multiple times in each heart cycle, and fibrillation takes the place of normal contraction. These phenomena are described in detail by Gregory W. Botteron and Joseph M. Smith in an article entitled, "A Technique for Measurement of the Extent of Spatial Organization of Atrial Activation During Atrial Fibrillation in the Intact Human Heart," in IEEE Transactions on Biomedical Engineering, 12 (June 1995), pages 579-586, and in a second article entitled, "Quantitative Assessment of the Spatial Organization of Atrial Fibrillation in the Intact Human Heart," in Circulation 93 (Feb. 1, 1996), pages 513-518. Both of these articles are incorporated herein by reference.

Invasive cardiac ablation techniques for the treatment of arrhythmias such as described above are well known in the art. For example, U.S. Pat. Nos. 5,443,489 and 5,480,422, issued to Ben-Haim describe systems for ablating cardiac tissue. U.S. Pat. No. 5,807,395, issued to Mulier et al., and U.S. Pat. No. 6,190,382, issued to Ormsby et al., describe systems for ablating body tissue using radiofrequency energy. U.S. Pat. Nos. 6,251,109 and 6,090,084, issued to Hassett et al., 6,117,101, issued to Diederich et al., 5,938,660 and 6,235,025, issued to Swartz et al., 6,245,064, issued to Lesh et al., 6,164,283, 6,305,378 and 5,971,983, issued to Lesh, 6,004,269, issued to Crowley et al., and 6,064,902, issued to Haissaguerre et al., describe apparatus for tissue ablation to treat atrial arrhythmia. U.S. Pat. No. 5,366,490, issued to Edwards et al., describes a method for applying destructive energy to a target tissue using a catheter.

Radiofrequency ablation using multiple contiguous circumferential points, guided by electro-anatomical mapping is proposed in the document, *Circumferential Radiofrequency Ablation of pulmonary Vein Ostia: A New Anatomic Approach for Curing Atrial Fibrillation*, Pappone C, et al., Circulation 102:2619-2628 (2000).

U.S. Pat. No. 6,743,225, issued to Sanchez et al., proposes to measure electrical activity of the cardiac tissue proximate a lesion site during an ablation treatment, and then to compare the measurements in order to determine whether the lesion is clinically efficacious so as to be able to block myocardial propagation. For example, the standard deviation of the amplitude of the electrocardiogram signal has been used as a metric.

U.S. Pat. No. 5,954,665, issued to Ben-Haim, the disclosure of which is herein incorporated by reference, describes a cardiac catheter having two electrodes, spaced apart. In operation, there is a measurable propagation delay between activation signals at the two electrodes under conditions of normal conduction. The catheter is manipulated so as to position the ablation device in contact with the endocardium at the site of a suspected abnormal conduction path. First and second pre-ablation signals, responsive to the heart's activation signals, are received from the two electrodes, respectively, preferably simultaneously, or alternatively successively. A correlation coefficient of the first and second pre-ablation signals is computed. An ablation device is then activated so as to ablate the endocardium at the site, preferably by applying radiofrequency energy thereto. After the ablation is completed, and the ablation device is deactivated, first and second post-ablation signals are respectively received from the first and second electrodes, and the correlation coefficient is again computed. If the pre- and post-ablation correlation coefficients are substantially the same, the ablation is determined to have been insufficient to interrupt the abnormal conduction path. If the post-ablation correlation coefficient is substantially less than or greater than the pre-ablation coefficient, however, the ablation is considered to have been effective in interrupting the abnormal path.

It has also been proposed to produce circumferential ablative lesions using ultrasound delivered through a balloon. This technique is described, for example, in the document, *First Human Experience With Pulmonary Vein Isolation Using a Through-the-Balloon Circumferential Ultrasound Ablation System for Recurrent Atrial Fibrillation*, Natale A, et al., Circulation 102:1879-1882 (2000).

SUMMARY OF THE INVENTION

It is often difficult to determine the proper dosage of energy, e.g., radiofrequency energy, that should be applied in an ablation procedure in order to achieve the desired result. When the dosage is insufficient, the non-conducting lesion does not extend deeply enough through the heart wall to disrupt the abnormal conduction, so that arrhythmia may persist or return after the procedure is completed. On the other hand, excessive dosage may cause dangerous damage to the tissue at and around the ablation site. The proper dosage is known to vary from case to case depending on various factors, such as catheter geometry, thickness of the heart wall, quality of the electrical contact between the catheter electrode and the heart wall, and blood flow in the vicinity of the ablation site. Blood flow carries away heat generated by the radiofrequency energy.

A safe, simple method for monitoring ablation progress in near real time is provided by disclosed embodiments of the invention, in which capture of a pacing signal is evaluated while ablation energy is concurrently directed to a target site. Using this technique, a practitioner can determine when a sufficient lesion has been created without interrupting the ablation procedure. The same catheter and electrode that are used for ablation are simultaneously used to test pacing capture. According to aspects of the invention, the practitioner immediately knows when to stop ablating, indicated by loss of capture of a pacing signal at a predetermined maximum voltage. Thus, the danger of excessive ablation is mitigated.

An embodiment of the invention provides a method for ablating tissue within a heart of a subject, which is carried out by inserting a probe into a chamber of the heart, disposing the probe in proximity to a target in the chamber for ablation of the target, pacing the heart by transmitting a pacing signal through the probe, and directing energy from the probe toward the target to ablate tissue therein until the pacing signal is no longer captured in the heart.

In one aspect of the method, pacing the heart and directing energy from the probe are performed simultaneously.

In a further aspect of the method, pacing the heart and directing energy from the probe are iteratively performed in alternation.

Yet another aspect of the method includes determining whether the pacing signal is captured following each performance of pacing the heart.

In an aspect of the method, directing energy comprises conducting an energy signal through the probe on a common channel with the pacing signal.

According to still another aspect of the method, the pacing signal and the energy signal have different frequencies.

According to a further aspect of the method, the energy is radiofrequency energy.

In yet another aspect of the method, after the pacing signal is no longer captured in the heart, the magnitude of the pacing signal is increased until the pacing signal is recaptured in the heart, after which the step of directing energy is performed a second time.

An additional aspect of the method is carried out after disposing the probe by monitoring temperature in the vicinity of the target.

One aspect of the method is carried out after disposing the probe by monitoring an electrical activation map of the heart.

Yet another aspect of the method includes obtaining an ultrasound image of the target through the probe while directing energy to the target.

An embodiment of the invention provides a cardiac ablation system, including a catheter adapted for insertion into a heart, and having a distal tip and a distally disposed electrode thereon. The system includes a first generator for producing a pacing signal, a second generator for producing an ablation energy signal, a conductor in the catheter for transmitting the pacing signal and the ablation energy signal to the electrode, and a monitor operative to provide an indication of capture of the pacing signal by the heart while the ablation energy signal is being applied to the electrode.

The cardiac ablation system may include a position sensor in the catheter, and electrical circuitry linked to the position sensor for determining a location of the distal tip of the catheter within the heart. The electrode can be exactly one common electrode for conducting the pacing signal and the ablation energy signal.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Embodiment 1

Figure 1:
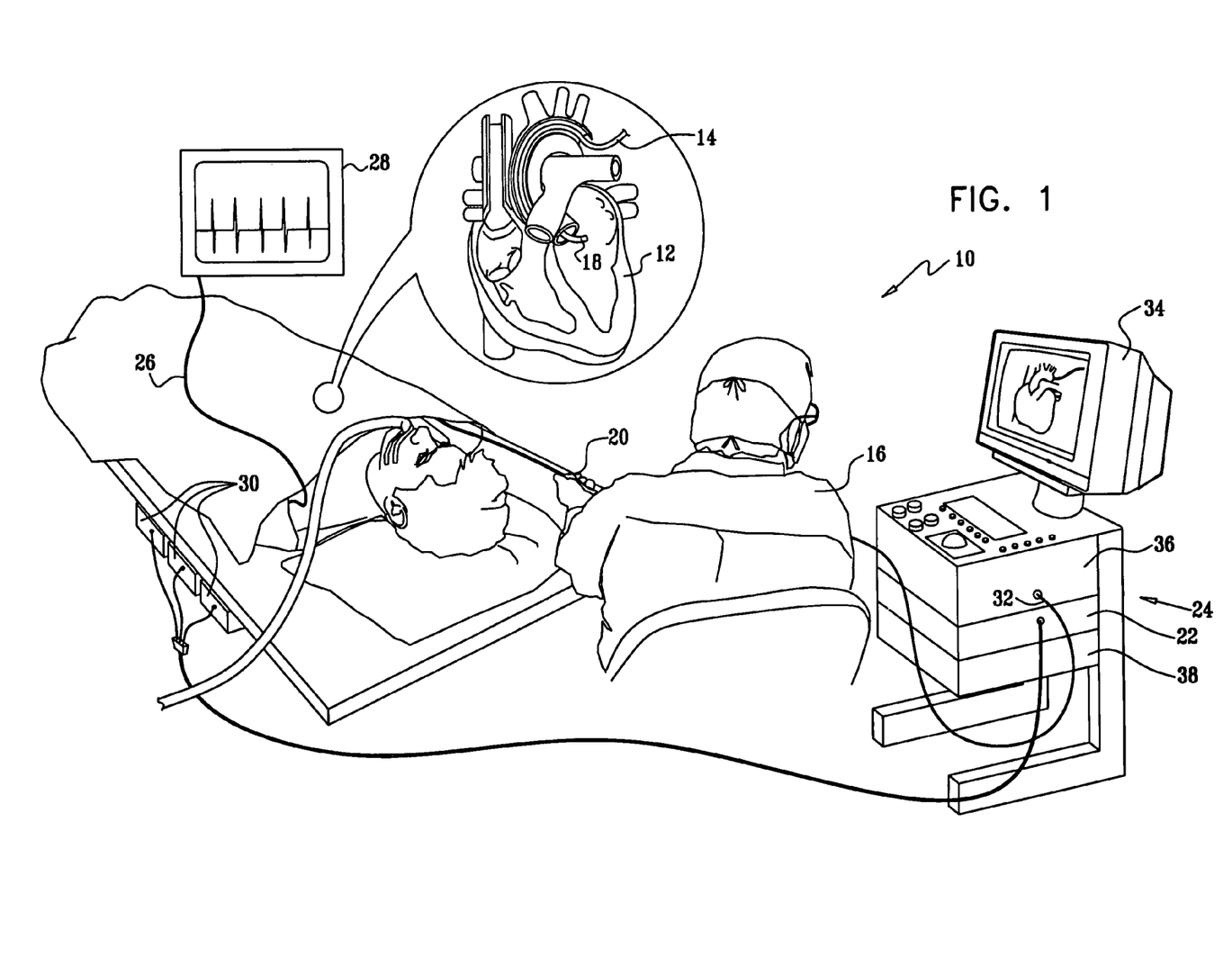
FIG. 1 is a pictorial illustration of a system for performing ablative procedures on a heart of a living subject in accordance with a disclosed embodiment of the invention.

Turning now to the drawings, reference is initially made to FIG. 1, which is a pictorial illustration of a system 10 for performing ablative procedures on a heart 12 of a living subject in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be ablated. Radiofrequency electrical current is then conducted through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia.

The catheter 14 typically comprises a handle 20, having suitable controls to enable the operator 16 to steer, position and orient the distal tip 18 of the catheter as desired during the ablation. To aid the operator 16, the distal portion of the catheter 14 contains position sensors (not shown) that provide signals to a positioning processor 22, located in a console 24. ECG electrodes (not shown) on the patient's body surface conduct electrical signals via a cable 26 to an ECG monitor 28. The catheter 14, may be adapted, *mutatis mutandis*, from the ablation catheter described in commonly assigned U.S. Pat. No. 6,669,692, whose disclosure is herein incorporated by reference.

The positioning processor 22 is an element of a positioning subsystem that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem comprises a magnetic position tracking system that determines the position and orientation of the catheter 14. The positioning subsystem generates magnetic fields in a predefined working volume, and senses these fields at the catheter. The positioning subsystem typically comprises a set of external radiators, such as field generating coils 30, which are located in fixed, known positions external to the patient. The coils 30 generate fields, typically electromagnetic fields, in the vicinity of the heart 12.

In an alternative embodiment of the positioning subsystem, a radiator in the catheter 14, such as a coil, generates electromagnetic fields, which are received by sensors (not shown) outside the patient's body.

The position sensor in the catheter 14 (not shown) transmits, in response to the sensed fields, position-related electrical signals over a cable 32 running through the catheter 14 to the console 24. Alternatively, the position sensors in the catheter 14 may transmit signals to the console 24 over a wireless link, as described in U.S. Patent Application Publication Nos. 2003/0120150 and 2005/0099290, the disclosures of which are herein incorporated by reference. The positioning processor 22 calculates the location and orientation of the catheter 14 based on the signals sent by the position sensor. The positioning processor 22 typically receives, amplifies, filters, digitizes, and otherwise processes signals from the catheter 14. The positioning processor 22 also provides a signal output to a display 34 that provides a visual indication of the position of the distal tip 18 of the catheter 14 relative to the site chosen for ablation.

Some position tracking systems that may be used for this purpose are described, for example, in U.S. Pat. Nos. 6,690,963, 6,618,612 and 6,332,089, and U.S. Patent Application Publications 2002/0065455, 2004/0147920, and 2004/0068178, whose disclosures are all incorporated herein by reference. Although the positioning subsystem shown in FIG. 1 uses magnetic fields, the methods described below may be implemented using any other suitable positioning subsystem, such as systems based on electromagnetic fields, acoustic or ultrasonic measurements.

Alternatively, the system 10 can be realized as the Carto-Biosense® Navigation System, available from Biosense Webster, Inc., 3333 Diamond Canyon Road, Diamond Bar, Calif. 91765, suitably modified to execute the procedures described herein.

Embodiments of the present invention combine simultaneous ablation and pacing so that an ablation lesion can be assessed in near real time, without interrupting the procedure. For this purpose, the console 24 includes a radiofrequency power source 36 that generates a radiofrequency ablation power signal. A power output of 50 watts at a frequency of 13.56 MHz is suitable. The console 24 is provided with a low frequency pacing generator 38 that produces a cardiac pacing signal. The pacing generator 38 typically has circuitry for varying its output voltage under control of the operator 16, e.g., from 3-6 volts, while maintaining a constant current output. Alternatively, the pacing generator 38 may maintain a constant voltage, while varying its current output. The outputs of the radiofrequency power source 36 and the pacing generator 38 are conducted to the catheter 14 via the cable 32.

Figure 2:
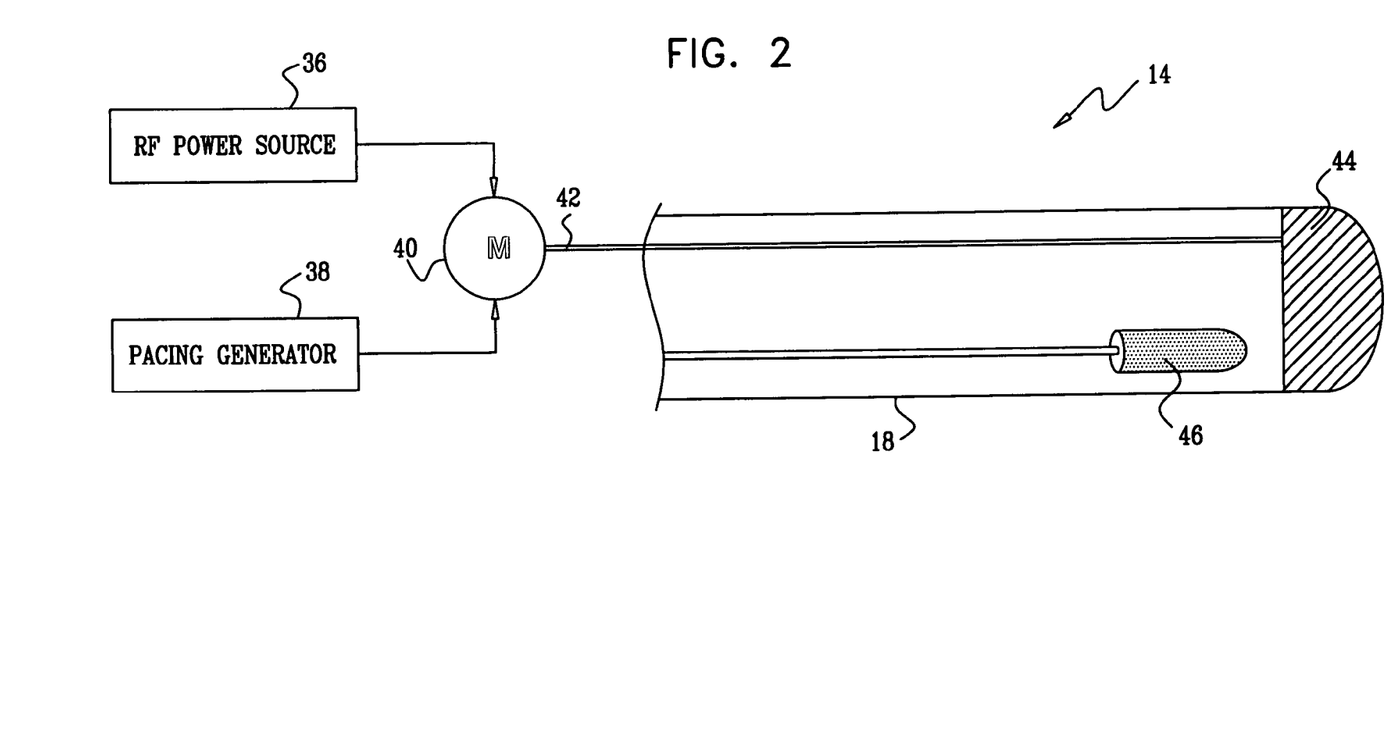
FIG. 2 is a block diagram of a portion of the system shown in FIG. 1, in which the output of a radiofrequency power source is mixed with a pacing signal, in accordance with a disclosed embodiment of the invention.

Reference is now made to FIG. 2, which is a block diagram of a portion of the system 10 (FIG. 1) in which the output of the radiofrequency power source 36 is mixed with the pacing signal produced by the pacing generator 38 in a mixer 40, in accordance with a disclosed embodiment of the invention. Since the radiofrequency and pacing signals are at different, widely spaced frequencies, the pacing signal does not substantially affect the ablation power, and the ablation signal has no effect on pacing of the heart. The combined waveform is conducted through the catheter 14 along a wire 42 that acts as a common channel for the combined waveform. The combined waveform is applied to a common electrode 44 at the distal tip 18 of the catheter 14 to simultaneously pace the patient's heart and deliver ablation energy to the target. The electrode 44 can be constructed in accordance with U.S. Patent Application Publication No. 2004/0158141, of common assignee herewith, and herein incorporated by reference. The ECG monitor 28 (FIG. 1) indicates whether the heart has actually captured the pacing signal. A position sensor 46 is typically located within the distal tip 18, adjacent to the electrode 44. The position sensor 46 can be an ultrasound position sensor of the type described in U.S. Pat. No. 6,751,492, issued to Ben-Haim, the disclosure of which is herein incorporated by reference.

Alternatively, the output of the radiofrequency power source 36 can be interlaced with the output of the pacing generator 38. In this mode of operation, the radiofrequency power source 36 is periodically disabled for a short time, typically 5-60 milliseconds. During this interval, the pacing generator 38 is operative to generate a pacing signal.

As a further alternative, the radiofrequency power source 36 remains disabled for a period of time, during which the pacing generator 38 is enabled for a period that is sufficiently long for a determination to be made, automatically or by the operator, whether the pacing signal has been captured. After this determination, the radiofrequency power source 36 is re-enabled if additional ablation is necessary.

Although the electrode 44 is shown as a single electrode as shown in FIG. 2, the catheter 14 may comprise any number of electrodes in any form. For example, the catheter 14 may comprise two or more ring electrodes, a plurality or array of point electrodes, or any combination of these types of electrodes for performing the therapeutic functions described herein.

Monitoring Ablation

The approach taken according to embodiments of the invention for assessing the extent of lesions created by ablation is to attempt to pace the heart concurrently with ablation through an electrode that is applied to the ablated region. If the pacing signal is "captured", i.e., the heartbeat synchronizes with the pacing signal, then lesion formation is considered to be incomplete. In the past it was necessary to stop the ablation procedure in order to test for capture of the pacing signal, and then resume the procedure afterwards if it was determined that further ablation was required.

Figure 3:
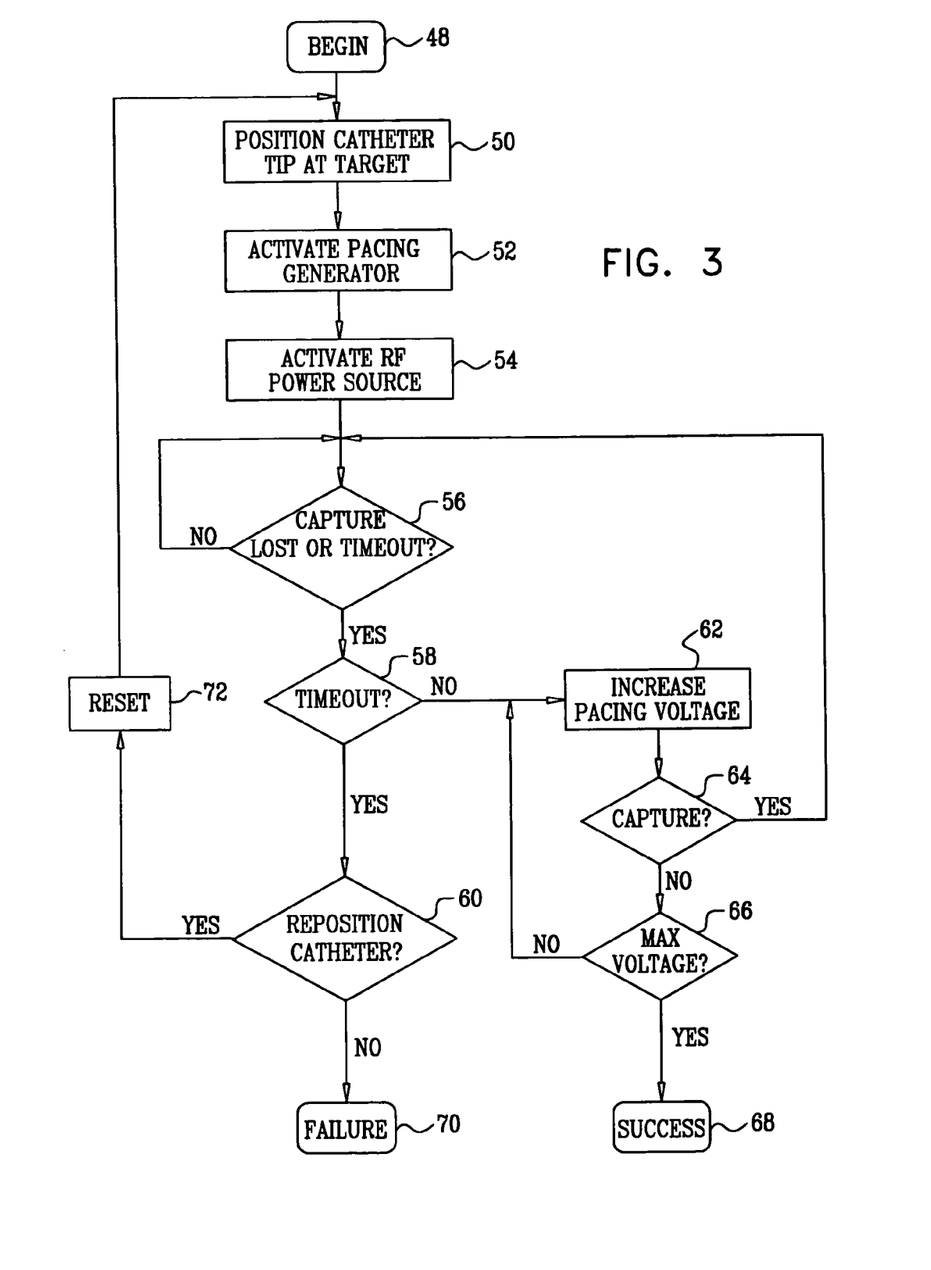
FIG. 3 is a flow chart illustrating a method of assessing a lesion formed by intracardiac ablation in accordance with a disclosed embodiment of the invention.

Reference is now made to FIG. 3, which is a flow chart illustrating a method of assessing a lesion formed by intracardiac ablation in accordance with a disclosed embodiment of the invention. At initial step 48, the operator introduces the catheter 14 (FIG. 1) into the heart conventionally.

Next, at step 50, the operator positions the distal tip 18 at the target site, using position indications provided by the display 34 to navigate the catheter within the cardiac chambers.

Next, at step 52, the operator activates the pacing generator 38 and increases the pacing voltage until the pacing signal is captured.

Next, at step 54, the radiofrequency power source 36 is activated, and the operator begins to ablate tissue at the target site.

Next, at delay step 56 it is expected that a lesion forms in the wall of the heart 12. Ablation continues until one of the following events has occurred: (1) the extent of the lesion is such that the pacing signal is no longer captured or (2) a timeout interval has been exceeded, typically 10 cycles. The timeout interval is not critical, and a range of 2-10 cardiac cycles is suitable.

Control now proceeds to decision step 58, where it is determined if a timeout has occurred. If the determination at decision step 58 is affirmative, then control proceeds to decision step 60, which is described below.

If the determination at decision step 58 is negative, then control proceeds to step 62, where the pacing voltage is increased. The increment is generally based on the experience of the operator and the condition of the patient. Prior to ablation the pacing threshold for capture is typically in a range of 0.3-1.0 mA. After ablation the pacing threshold may rise to about 10 mA. Initially a relatively large increment is used in step 62, approximately 0.5 mA, in order to quickly locate the pacing threshold. Later in the procedure the increment may be reduced to about 0.1 mA.

Control now proceeds to decision step 64, where it is determined if the pacing signal has been recaptured as a result of the increase in pacing signal strength. If the determination at decision step 64 is affirmative, then control returns to delay step 56, and the ablation continues.

If the determination at decision step 64 is negative, then control proceeds to decision step 66, where it is determined if a predetermined maximum level has been reached. When constant current pacing is used, the maximum value is typically set at about 2-3 times the level of the initial pacing threshold. For example, if the initial threshold is 0.5 mA, ablation may be considered to be complete once the threshold rises to 1.5 mA. If the determination at decision step 64 is negative, then control returns to step 62.

If the determination at decision step 64 is affirmative, then it is concluded that the extent of the lesion created by the ablation is sufficient. The procedure is terminated successfully at final step 68 and then terminated. Of course, when re-entrant loops or other abnormal conduction paths are complex, the sequence beginning at step 50 can be iterated at another target site.

Decision step 60 is performed if the determination at decision step 58 is affirmative. At this point, it has not been possible to interrupt capture of the pacing signal by ablation. The operator now decides whether to reposition the catheter and make further attempts at ablation. If the determination at decision step 60 is negative, then the procedure is declared to be unsuccessful and terminated at final step 70.

If the determination at decision step 60 is affirmative, then control proceeds to step 72, where the radiofrequency power source 36 and pacing generator 38 are reset. Control then returns to step 50 for adjustment in the position of the distal tip 18.

Embodiment 2

Figure 4:
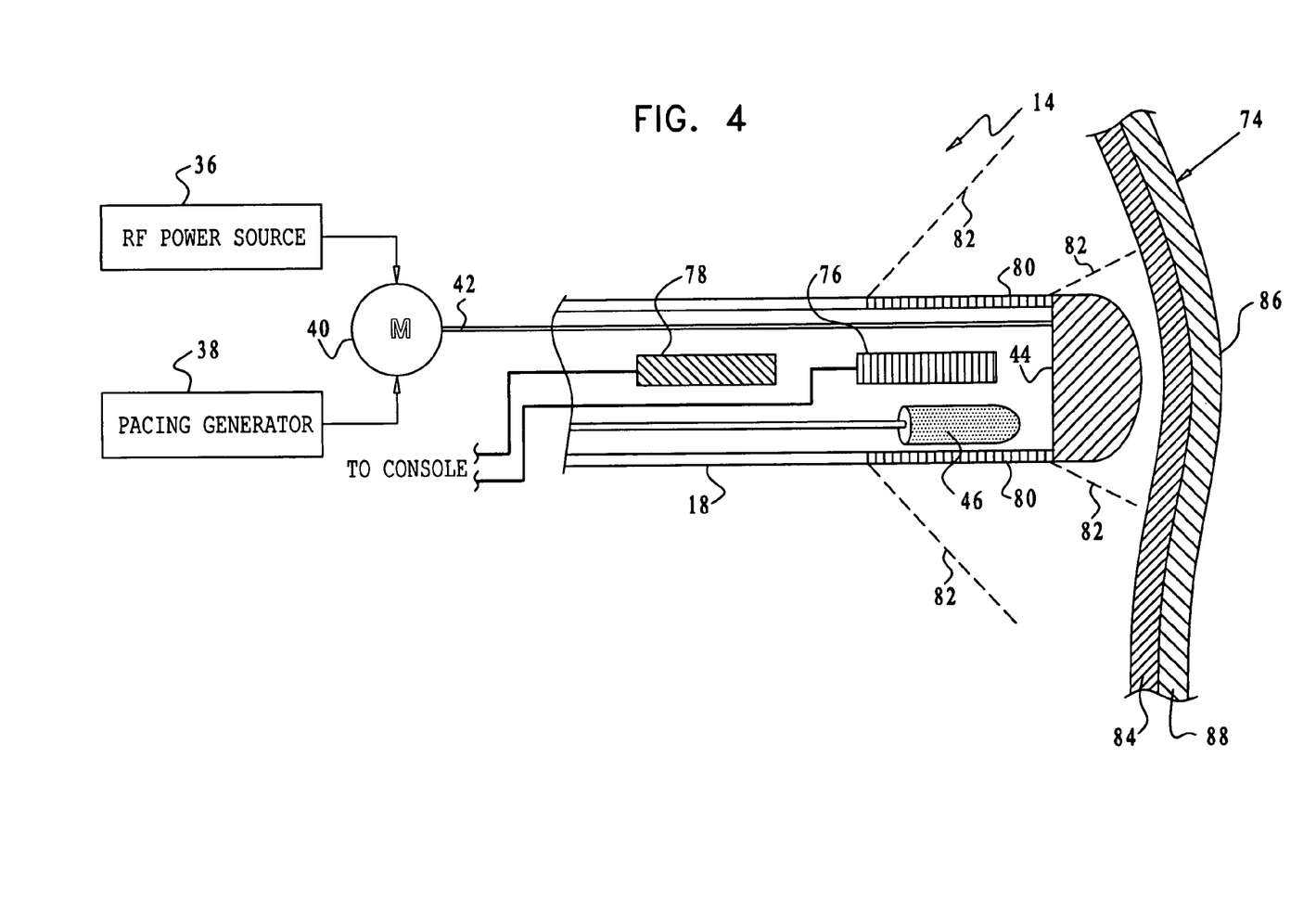
FIG. 4 is a schematic of the distal tip of a catheter for use in the system shown in FIG. 1 in accordance with an alternate embodiment of the invention.

The method disclosed above with reference to FIG. 2 may be combined with other lesion assessment techniques. Reference is now made to FIG. 4, which is a schematic of the distal tip 18 of the catheter 14 (FIG. 1) in accordance with an alternate embodiment of the invention. The distal tip 18, shown in juxtaposition to target tissue 74, is now provided with an array of ultrasound transducers 76 and a temperature sensor 78, for additional lesion production and assessment as described, for example, in U.S. Pat. Nos., 5,443,489, 6,321,109, 6,083,170, 6,301,496 and U.S. Patent Application Publication Nos. 2004/0143258 and 2004/0147920, whose disclosures are herein incorporated by reference. The transducers 76 and the temperature sensor 78 are connected to suitable signal processing circuitry in the console 24 (FIG. 1), which can be realized as the above-noted Carto-Biosense Navigation System. Lesion assessment may be conducted simultaneously using feedback from electrical obtained using the electrode 44 and local temperature information obtained from the temperature sensor 78 in conjunction with information obtained using the transducers 76.

The transducers 76 are typically realized as a phased array. In this embodiment a segment 80 of the wall of the catheter that generally opposes the transducers 76 is sonolucent, so that the transducers 76 have a field of view 82 directed generally forward, as indicated by broken lines. As the electrode 44 is solid, transfer of energy to the target tissue occurs efficiently. However, when using this embodiment, it may be necessary to adjust the position of the distal tip 18 in order to bring the ablation site into the field of view 82.

Alternatively, a 2-dimensional array of transducers, or even a single element transducer can be used. The transducers 76 may be forward looking or have other directional characteristics, for example they may be side looking, or could even be omnidirectional. Typically, the array comprises at least ten transducers, each of which is no more than 0.5 mm across. The console 24 drives the transducers 76 at a high frequency, typically in the range of 5-15 MHz. An array of sixteen transducers under these conditions, for example, is capable of producing images (including Doppler images) of tissue with a resolution of about 0.1 mm. The transducers 76 may be used in this manner to determine the thickness and other qualities of the target tissue 74 prior to ablation, and to assess the progress and results of the ablation procedure.

In one embodiment, the transducers 76 can be used to determine the temperature of the target tissue 74 as a measure of the extent of ablation, in addition to or instead of temperature measurements that may be made by the temperature sensor 78. To determine the temperature, the propagation speed of ultrasonic waves in a surface layer 84 is assessed, by measuring the round-trip time of the waves that are reflected from a far surface 86 of the target tissue 74 and which then return to the transducers 76. Generally, the propagation speed of the ultrasonic waves increases with tissue temperature. In water, for example, the speed of ultrasonic waves varies by about 2 m/s per degree. Therefore, a temperature increase is perceived as a thinning of the surface layer 84, relative to underlying layers, as the ultrasonic waves are reflected back to the transducers 76 in a shorter span of time. By measuring and comparing the apparent thickness of the target tissue 74 before and after applying radiofrequency ablation, the temperature changes in the tissue, and hence the extent of the ablation, can be assessed. When the transducers 76 emit and receive ultrasonic waves at frequencies in the range of 10-15 MHz, apparent thickness variations on the order of 0.1 mm or less may be detected in this manner, corresponding to temperature variations on the order of a few degrees.

As another example, the transducers 76 may be used to observe creation of microbubbles in the target tissue 74 due to cavitation during ablation. The number of microbubbles typically increases with the tissue temperature. The microbubbles can be most clearly observed by subtracting successive images formed by the transducers 76, wherein the orderly increase and decrease in the density of microbubbles over time can be used to distinguish the microbubbles from background noise in an ultrasonic image developed in the console 24 using known methods. The microbubble density thus observed gives a measure of the tissue temperature.

In still a further example, the transducers 76 may be used in a Doppler imaging mode to measure the speed of blood flow in a deeper layer 88 of the target tissue 74. Ablation of overlying layers, such as the surface layer 84, is expected to cause blockage of blood vessels within the deeper layer 88, thus causing changes in blood flow velocity. The extent of ablation is thus assessed by measuring the change in velocity resulting from the ablation procedure.

Alternatively or additionally, other methods for measuring tissue temperature and assessing the extent of ablated tissue may be used, as are known in the art. For example, the catheter 14 may comprise a miniature nuclear magnetic resonance (NMR) sensor (not shown), which can be used to map the extent of ablation in the vicinity of the catheter tip.

These techniques can be applied in many combinations in conjunction with assessment of pacing signal capture as described above. For example, a critical local temperature may be reached before maximum pacing voltage has been recognized at decision step 66 (FIG. 3). This could lead the operator to temporarily cease ablation to prevent charring of tissue. Alternatively, the information obtained using the transducers 76 might reveal sufficient disruption of tissue anatomy or blood flow to enable the procedure to be terminated early. For example, when an ultrasound transducer is used in combination with the pacing and ablation electrode, if the pacing and ablation electrode were touching the target tissue, the pacing electrode might not reach a level at which the procedure would be required to be halted. However, the ultrasound transducer would detect changes that would then trigger a halt to the procedure. Alternatively, if the catheter tip is not directed toward the target, the forward-looking ultrasound transducer would not detect progress of the ablation. Nevertheless, attainment of the pacing threshold would alert the operator to halt the procedure.

Embodiment 3

Figure 5:
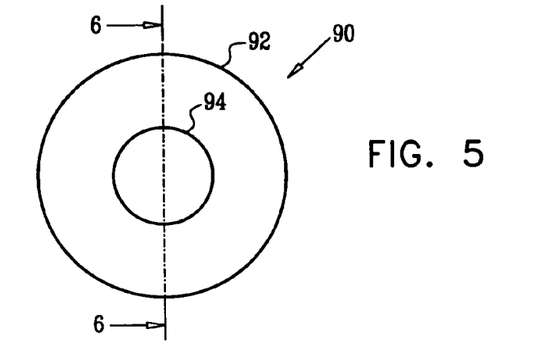
FIG. 5 is an end view of a distal portion of a catheter having a fenestrated tip, for use in the system shown in FIG. 1, in accordance with an alternate embodiment of the invention.

Reference is now made to FIG. 5, which is an end view of a distal portion 90 of a catheter suitable for use in the system 10 (FIG. 1), in accordance with an alternate embodiment of the invention. In this embodiment, the tip is provided with an ablation electrode 92 having a central aperture 94 measuring about 1-1.5 mm in diameter.

Figure 6:
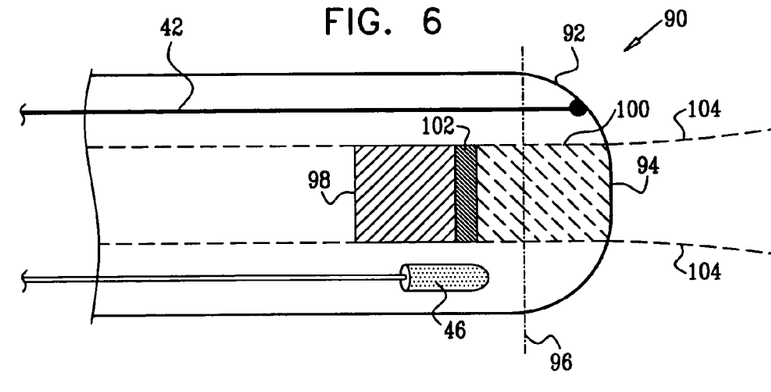
FIG. 6 is a sectional view taken along line 6-6 of the catheter shown in FIG. 5.

Reference is now made to FIG. 6, which is a sectional view taken along line 6-6 of the distal portion 90 of the catheter shown in FIG. 5. The electrode 92 extends a short distance behind the tip of the catheter, being delimited by a broken line 96. An ultrasound transducer 98 is positioned a short distance behind the aperture 94, being separated from the distal end of the catheter by a plug 100 of a sonolucent material such as silicon, and having an interface 102 with the plug 100. The transducer 98 is forward looking, and has a field of view 104, indicated by broken lines, with an operational range of about 8 mm. The field of view 104 extends through the aperture 94 and encompasses the target tissue, but transfer of energy is somewhat reduced due to reduction in the contact area of the electrode 92 as compared with the electrode 44 (FIG. 4).

Embodiment 4

Figure 7:
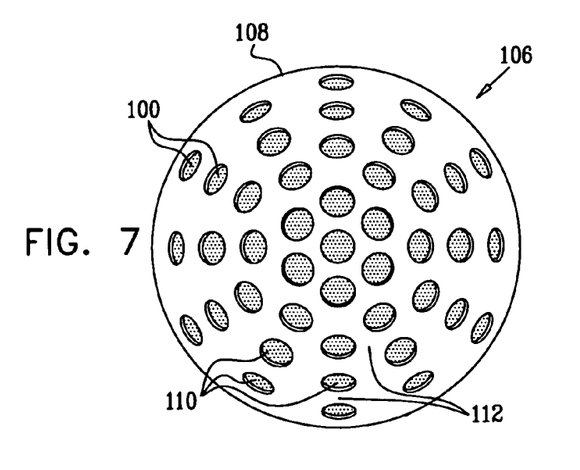
FIG. 7 is an end view of a distal portion of a catheter having a multiply fenestrated tip, for use in the system shown in FIG. 1, in accordance with an alternate embodiment of the invention.

Reference is now made to FIG. 7, which is an end view of a distal portion 106 of a catheter suitable for use in the system 10 (FIG. 1), in accordance with an alternate embodiment of the invention. The construction of this embodiment is similar to the distal portion 90 (FIG. 6). However, in this embodiment, the tip is provided with an ablation electrode 108 having multiple small perforations or fenestrations 110, measuring about 0.1 mm in diameter, that are separated by solid areas 112. Typically, there are about 75 fenestrations 110. However, the number is not critical. While round perforations are shown in the electrode 108 in FIG. 7, other shapes may be equally effective.

This embodiment has characteristics that are intermediate between the design shown in FIG. 4 and the design shown in FIG. 5 and FIG. 6. The solid areas 112 partially block the field of view of the transducer, but energy transfer from the electrode is increased, as compared with embodiment of FIG. 5. Furthermore, this embodiment has the advantage that the field of view of the transducer extends through the fenestrations 110 and includes the target area. Hence, there is no need to revise the position of the catheter tip to obtain an ultrasound image of the target during operation, as may be the case with the embodiment of FIG. 4.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:
1. A cardiac ablation system, comprising:
a catheter adapted for insertion into a heart, having a distal tip and a distally disposed electrode thereon;
a first generator for producing a pacing signal;
a second generator for producing an ablation energy signal;
a conductor in said catheter for transmitting said pacing signal and said ablation energy signal to said electrode for ablation of a specified area in said heart;
a monitor operative to provide an indication of a capture of said pacing signal by said heart while said ablation energy signal is being applied to said electrode for application to said specified area in said heart, the second generator configured to produce the ablation energy signal when the capture of said pacing signal occurs as a heartbeat synchronizes with said pacing signal, the second generator configured to stop production of the ablation energy signal when the capture of said pacing signal does not occur; and
a mixer for combining said pacing signal and said ablation energy signal to transmit said pacing signal and said ablation energy signal to said electrode simultaneously.

2. The cardiac ablation system according to claim 1, further comprising:
   a position sensor in said catheter, and
   electrical circuitry linked to said position sensor for determining a location of said distal tip in said heart.

3. The cardiac ablation system according to claim 1, wherein said electrode is exactly one common electrode for conducting said pacing signal and said ablation energy signal.

4. The cardiac ablation system according to claim 1, further comprising a temperature sensor in said catheter.

5. The cardiac ablation system according to claim 1, further comprising an ultrasound transducer in said catheter.

6. The cardiac ablation system according to claim 5, wherein said ultrasound transducer is a single element transducer.

7. The cardiac ablation system according to claim 5, wherein said ultrasound transducer is a phased array of ultrasound transducers.

8. The cardiac ablation system according to claim 5, wherein said ultrasound transducer is a 2-dimensional array of ultrasound transducers.

9. The cardiac ablation system according to claim 5, wherein said electrode has an aperture, wherein a field of view of said ultrasound transducer extends through said aperture.

10. The cardiac ablation system according to claim 5, wherein said electrode has a plurality of apertures, wherein a field of view of said ultrasound transducer extends through said apertures.

11. The cardiac ablation system according to claim 1, wherein said pacing signal and said ablation energy signal have different frequencies.

12. The cardiac ablation system according to claim 1, wherein said ablation energy signal is a radiofrequency signal.

13. The cardiac ablation system according to claim 1, wherein said monitor no longer indicates said pacing signal being captured in said heart, and the second generator increases a magnitude of said pacing signal until said pacing signal is recaptured in said heart.

* * * * *